United States Patent
Lee et al.

(10) Patent No.: US 10,395,775 B2
(45) Date of Patent: Aug. 27, 2019

(54) APPARATUS AND METHOD FOR RECOMMENDING OPERATION PATH

(71) Applicants: ELECTRONICS AND TELECOMMUNICATIONS RESEARCH INSTITUTE, Daejeon (KR); INDUSTRY-ACADEMIC COOPERATION FOUNDATION, YONSEI UNIVERSITY, Seoul (KR)

(72) Inventors: Jeong Won Lee, Daejeon (KR); Sung Hee Park, Daejeon (KR); Ji Wook Jeong, Daejeon (KR); Woo Jin Hyung, Seoul (KR); Soo Yeul Lee, Daejeon (KR); Jong Hyun Park, Daejeon (KR)

(73) Assignees: ELECTRONICS AND TELECOMMUNICATIONS RESEARCH INSTITUTE, Daejeon (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 957 days.

(21) Appl. No.: 14/940,670

(22) Filed: Nov. 13, 2015

(65) Prior Publication Data
US 2016/0300143 A1 Oct. 13, 2016

(30) Foreign Application Priority Data
Apr. 10, 2015 (KR) .......................... 10-2015-0051050

(51) Int. Cl.
*G06F 15/18* (2006.01)
*G16H 50/50* (2018.01)

(52) U.S. Cl.
CPC .................... *G16H 50/50* (2018.01)

(58) Field of Classification Search
CPC ............................................ G06T 2207/30101
(Continued)

(56) References Cited

U.S. PATENT DOCUMENTS

2005/0043614 A1* 2/2005 Huizenga ............... A61B 5/055
600/427
2010/0296709 A1* 11/2010 Ostrovsky-Berman ......................
G06T 7/11
382/128
(Continued)

FOREIGN PATENT DOCUMENTS

| KR | 10-2010-0098055 A | 9/2010 |
|----|-------------------|--------|
| KR | 10-2012-0046439 A | 5/2012 |
| KR | 10-1206340 B1 | 11/2012 |

OTHER PUBLICATIONS

Ji Wook Jeong et al., "Vessel Navigator for Surgical Rehearsal System Using Topological Map: An Application to Gastrectomy," ICSAI, Nov. 15, 2014, pp. 1-5.
(Continued)

*Primary Examiner* — David R Vincent

(57) ABSTRACT

The present disclosure provides an operation-path recommendation method and apparatus. In the present disclosure, by an operation-path recommendation apparatus, a blood vessel graph model is generated based on patient's anatomical information, a plurality of candidate paths between defined start and destination points is extracted; node information on at least one node in each of the candidate paths is extracted; a cost function is applied to each candidate path, based on the extracted node information.

6 Claims, 7 Drawing Sheets

(58) Field of Classification Search
USPC .................................................. 706/15, 45
See application file for complete search history.

(56) References Cited

U.S. PATENT DOCUMENTS

| | | | |
|---|---|---|---|
| 2010/0296718 A1* | 11/2010 | Ostrovsky-Berman | ..................... G06T 7/62 382/133 |
| 2012/0237094 A1* | 9/2012 | Kurihara | .............. G06K 9/4638 382/128 |
| 2013/0116551 A1 | 5/2013 | Florent et al. | |
| 2014/0066781 A1 | 3/2014 | Park et al. | |
| 2015/0187085 A1* | 7/2015 | Ihara | ........................ A61B 5/08 382/128 |

OTHER PUBLICATIONS

Jeong Won Lee et al., "Path Optimization Algorithm for Dissecting Variant Types of the Left Gastric Vein in Laparoscopic Gastrectomy", SIIM 2015, May 28-30, 2015, pp. 1-6, http://siim.org/?page=15ab_path_optimizati.

* cited by examiner

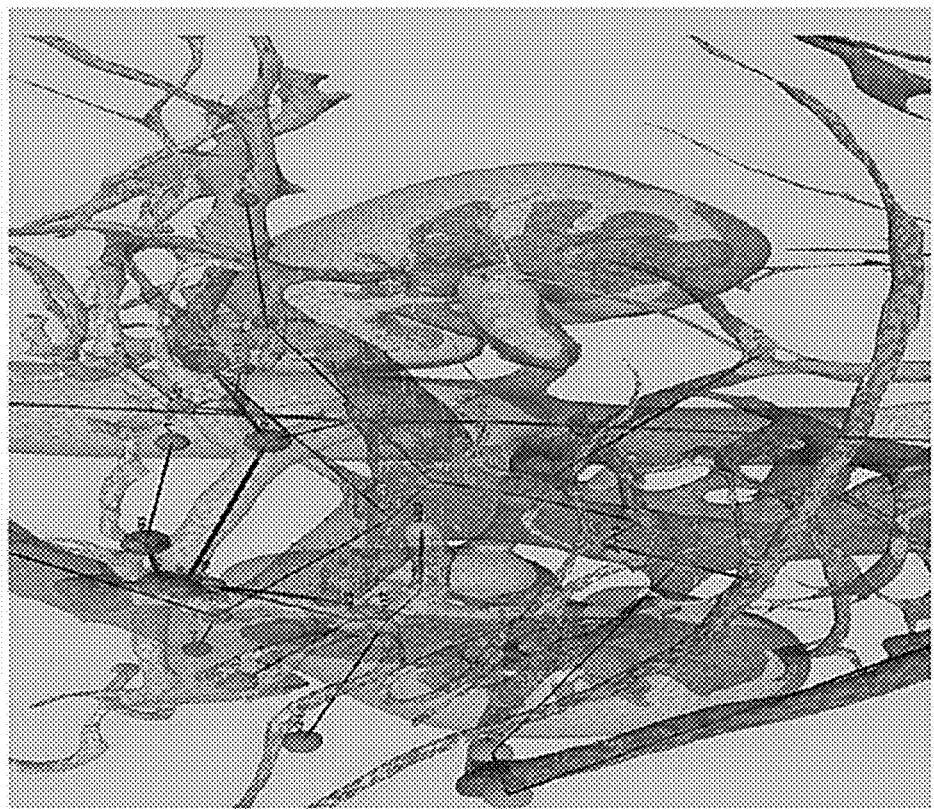
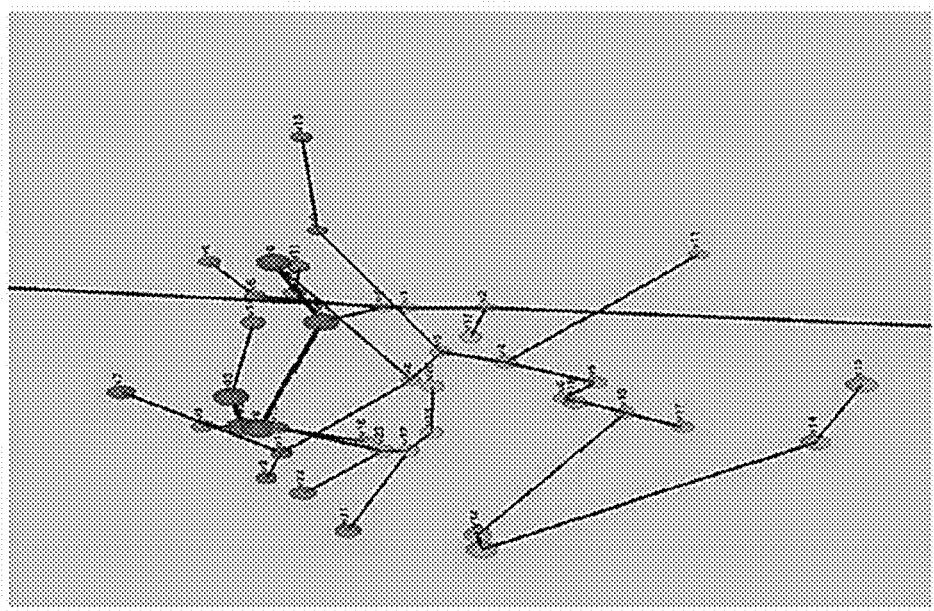

FIG. 6

| Type of LGV | Path | Number of branches on the path | Shortest distance between two transit points (mm) | Number of obstructing segments | Cost | Rank |
|---|---|---|---|---|---|---|
| 1 | 1 (Purple) | 2 | 4.13 | 1 | 24.13 | 6 |
|   | 2 (Orange) | 3 | 4.13 | 0 | 19.13 | 3 |
|   | 3 (Green) | 2 | 11.7 | 0 | 21.7 | 5 |
|   | 4 (Yellow) | 1 | 11.7 | 0 | 16.7 | 2 |
|   | 5 (Pink) | 2 | 10.07 | 0 | 20.07 | 4 |
|   | 6 (Gray) | 0 | 12.29 | 0 | 12.29 | 1 |
| 2 | 1 (Purple) | 4 | 4.13 | 2 | 44.13 | 5 |
|   | 2 (Orange) | 5 | 4.13 | 1 | 39.13 | 4 |
|   | 3 (Green) | 3 | 13.15 | 0 | 28.15 | 3 |
|   | 4 (Yellow) | 3 | 2.75 | 0 | 17.75 | 2 |
|   | 5 (Pink) | 2 | 5.4 | 0 | 15.4 | 1 |
|   | 6 (Gray) | 0 | 45.56 | 0 | 45.56 | 6 |
| 3 | 1 (Purple) | 5 | 4.13 | 2 | 49.13 | 6 |
|   | 2 (Orange) | 5 | 10.9 | 1 | 45.9 | 5 |
|   | 3 (Green) | 4 | 13.15 | 0 | 33.15 | 4 |
|   | 4 (Yellow) | 3 | 17.96 | 0 | 32.96 | 3 |
|   | 5 (Pink) | 2 | 3.65 | 0 | 13.65 | 1 |
|   | 6 (Gray) | 0 | 14.5 | 0 | 14.5 | 2 |
| 4 | 1 (Purple) | 5 | 10.87 | 1 | 45.87 | 5 |
|   | 2 (Orange) | 5 | 13.15 | 0 | 38.15 | 4 |
|   | 3 (Green) | 4 | 16.36 | 0 | 36.36 | 2 |
|   | 4 (Yellow) | 3 | 11.5 | 0 | 26.5 | 1 |
|   | 5 (Pink) | 5 | 22.6 | 0 | 47.6 | 6 |
|   | 6 (Gray) | 4 | 16.16 | 0 | 36.6 | 3 |

APPARATUS AND METHOD FOR RECOMMENDING OPERATION PATH

CROSS-REFERENCE TO RELATED APPLICATION

The present application claims a priority to a Korean patent application number 10-2015-0051050 filed on, Apr. 10, 2015, the entire disclosure of which is incorporated herein in its entirety by reference.

BACKGROUND

1. Field of Invention

The present disclosure relates to an operation-path recommendation method and apparatus, and, in particular, to an operation-path recommendation method and apparatus to generate a 'blood vessel graph model' based on patient's anatomical information, and to recommend an optimal operation path using the 'blood vessel graph model' and an associated 'cost function'.

2. Description of Related Art

An operation navigation technique may indicate positional, directional and/or the like data for a surgical operation. The operation navigation technique may provide the surgeon with underlying information for controlling a surgical instrument and thus may assist in enhancement in a surgical effect and reliability.

In a conventional operation navigation technique, positions of the operation instrument are tracked in a real time, and a positional relationship thereof with a target to be treated is image-displayed in an overlay manner. Further, in the conventional technique, in guiding an operation path, a current position of the operation instrument is detected and, then, a direction to move the instrument in a next step is determined based on the detected current position.

For this reason, it is disadvantageous that the conventional operation navigation technique may not be employed at a surgical planning step prior to the operation. Further, it has a limitation of not providing operation path information based on patient's anatomical data.

Thus, there is a need for a novel operation navigation technique to solve the above.

The present disclosure is made based on the above-mentioned technical situations. It may be appreciated that the present disclosure is not only to satisfy the above need but also to provide further technical features not devised easily by the skilled person to the art.

SUMMARY

The present disclosure may provide, in one purpose thereof, an operation-path recommendation method to recommend an optimal operation path for the surgeon, by generating a blood vessel graph model based on patient's anatomical information; extracting a plurality of candidate paths for a specific surgical operation, based on the generated blood vessel graph model; and applying a cost function to each of the extracted candidate paths.

It may be appreciated that the present disclosure should not be limited to the above purpose with respect to technical contributions thereof, but, different contributions from the above may be achievable from following details of the present disclosure by the skilled person to the art.

In one aspect of the present disclosure, an operation-path recommendation method is provided, the method (a) by an operation-path recommendation apparatus, generating a blood vessel graph model based on patient's anatomical information; (b) by the operation-path recommendation apparatus, extracting a plurality of candidate paths, each path running between defined start and destination points; (c) by the operation-path recommendation apparatus, extracting node information on at least one node in each of the candidate paths; an (d) by the operation-path recommendation apparatus, applying a cost function to each candidate path, based on the extracted node information.

In one embodiment, the (a) may include (a1) by the operation-path recommendation apparatus, loading patient's image data thereon; (a2) by the operation-path recommendation apparatus, generating a 3-dimensional (3D) model for the patient's anatomical information, based on the patient's image data; and (a3) by the operation-path recommendation apparatus, generating the blood vessel graph model based on the 3D model.

In one embodiment, the (a3) may include reflecting, by the operation-path recommendation apparatus, viewpoint information of an imaging device imaging the patient's image data.

In one embodiment, the (b) may include, by the operation-path recommendation apparatus, defining start and destination points associated with a specified surgical operation; and by the operation-path recommendation apparatus, extracting the plurality of candidate paths on the blood vessel graph model, each path running between the defined start and destination points.

In one embodiment, the node information may include a number and/or type of the at least one node in each candidate path.

In one embodiment, the node information may include a number of jump nodes, branch nodes, and/or cross nodes in each candidate path.

In one embodiment, the jump node may refer to a node where a transfer between an artery and a vein occurs, the branch node may refer to a node where a plurality of blood vessel is directly coupled to one another, and the cross node may refer to a node where one blood vessel is not visible from a viewpoint of a medical imaging device due to its overlapping with another blood vessel.

In one embodiment, the (d) may include (d1) by the operation-path recommendation apparatus, calculating cost values for the plurality of candidate paths respectively, the calculating reflecting a number and/or type of at least one node in each candidate path; and (d2) by the operation-path recommendation apparatus, specifying a candidate path with the lowest cost value from among the plurality of candidate paths.

In one embodiment, the (d) may include applying a weight factor to a cost value for each candidate path, the weight factor being dependent on a type of a node in each candidate path, the node type including jump, branch, and/or cross nodes.

In one aspect of the present disclosure, there is provided an electronic machine-readable storage medium including a program therein, the program being configured to, when executed by an electronic machine, cause the machine to perform an operation-path recommendation method as defined above. Further, the program may be distributed in a wired or wireless manner.

In one aspect of the present disclosure, an operation-path recommendation apparatus is provided, the apparatus including an anatomical information manager configured to manage patient's anatomical information; and an operation path manager. The operation path manager may be configured to generate a blood vessel graph model based on the anatomical information; to extract a plurality of candidate paths between defined start and destination points; to extract node information on at least one node in each of the extracted candidate paths; and to apply a cost function to each candidate path based on the extracted node information.

In one embodiment, the anatomical information manager may be further configured to manage image data representing the patient's anatomical information, wherein the operation path manager may be further configured to generate a 3D model for the patient's anatomical information based on the patient's image data, and to generate the blood vessel graph model based on the generated 3D model.

In one embodiment, the operation path manager may be further configured to define the start and destination points associated with a selected specific surgical-operation, and to extract, on the blood vessel graph model, the plurality of candidate paths between the defined start and destination points.

In one embodiment, the operation path manager may be further configured to extract a number of and/or a type of at least one node in each of the extracted candidate paths.

In one embodiment, the operation path manager may be further configured to calculate cost values corresponding to the candidate paths respectively, using a number of and/or a type of at least one node in each of the extracted candidate paths, and to specify and recommend at least one candidate path with the lowest cost value from among the plurality of candidate paths.

The present disclosure may recommend an optimal operation path based on the patient's anatomical information. Specifically, the present disclosure may generate the blood vessel graph model based on the patient's anatomical information, and recommend an optimal operation path based on the generated blood vessel graph model. This may provide optimal operation path recommendations taking into account the patient's anatomical information.

Further, the present disclosure may quantify a stress level expected for the surgeon to undergo for each of the candidate operation-paths, and then may recommend an optimal operation path based on the quantified stress level. This may provide optimal operation path recommendations with a minimum stress level for the surgeon (for example, the stress may include a recognition-related stress, a time-related stress, a risk-related stress, etc.). Specifically, the present disclosure may extract a plurality of candidate paths for the specific surgical-operation, quantify a stress level (e.g., in form of a cost value) corresponding to each candidate path using the cost function, and then recommend an optimal operation path based on the quantified stress level. This may provide the operation path recommendations with a minimum stress level for the surgeon.

Additionally, the present disclosure may reflect variables dependent on the blood vessel graph model in applying the cost function, to lead to more accurate calculation of the stress level for each candidate path. To be specific, the present disclosure may take into account a number of and/or a type of nodes in the blood vessel graph model to calculate the cost value. This may lead to finer calculations of the stress level.

It may be noted that the advantages of the present disclosure are not limited to the above, but another benefits may be apparently available to the skilled person to the art without departing from the spirit and scope of the present disclosure.

BRIEF DESCRIPTION OF THE DRAWINGS

FIGS. 3A and 3B are illustrations of example blood vessel graph models generated based on the 3D model.

FIG. 6 is a table representing cost values corresponding respectively to the operation path recommendations as in FIGS. 5A, 5B, 5C, and 5D.

DETAILED DESCRIPTIONS

Figure 1:
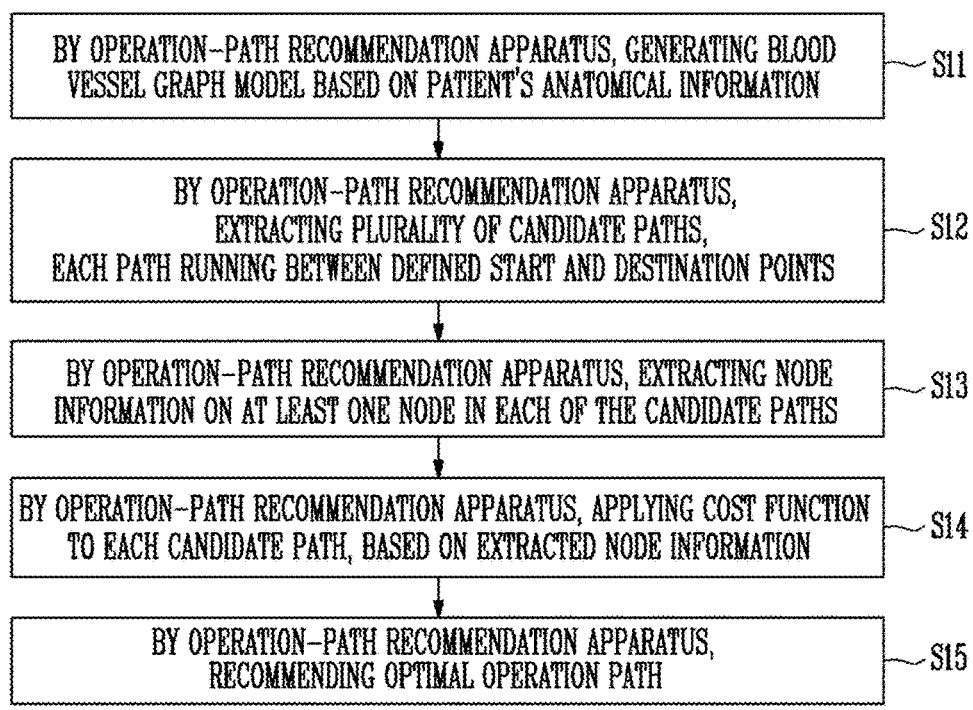
FIG. 1 is a flow diagram of an operation-path recommendation method, according to one embodiment of the present disclosure.
Figure 2A:
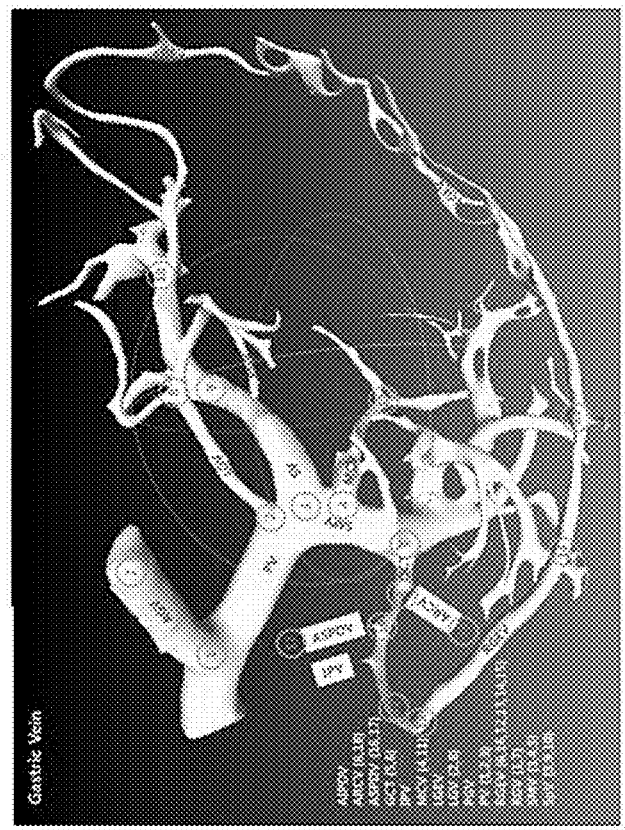
FIGS. 2A and 2B are illustrations of example 3D models generated based on patient's anatomical information.
Figure 2B:
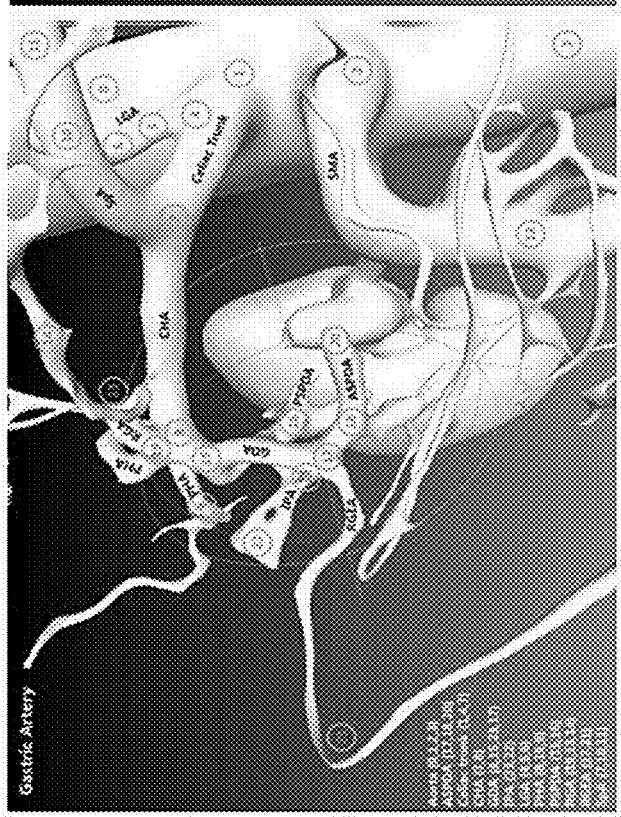
Figure 4:
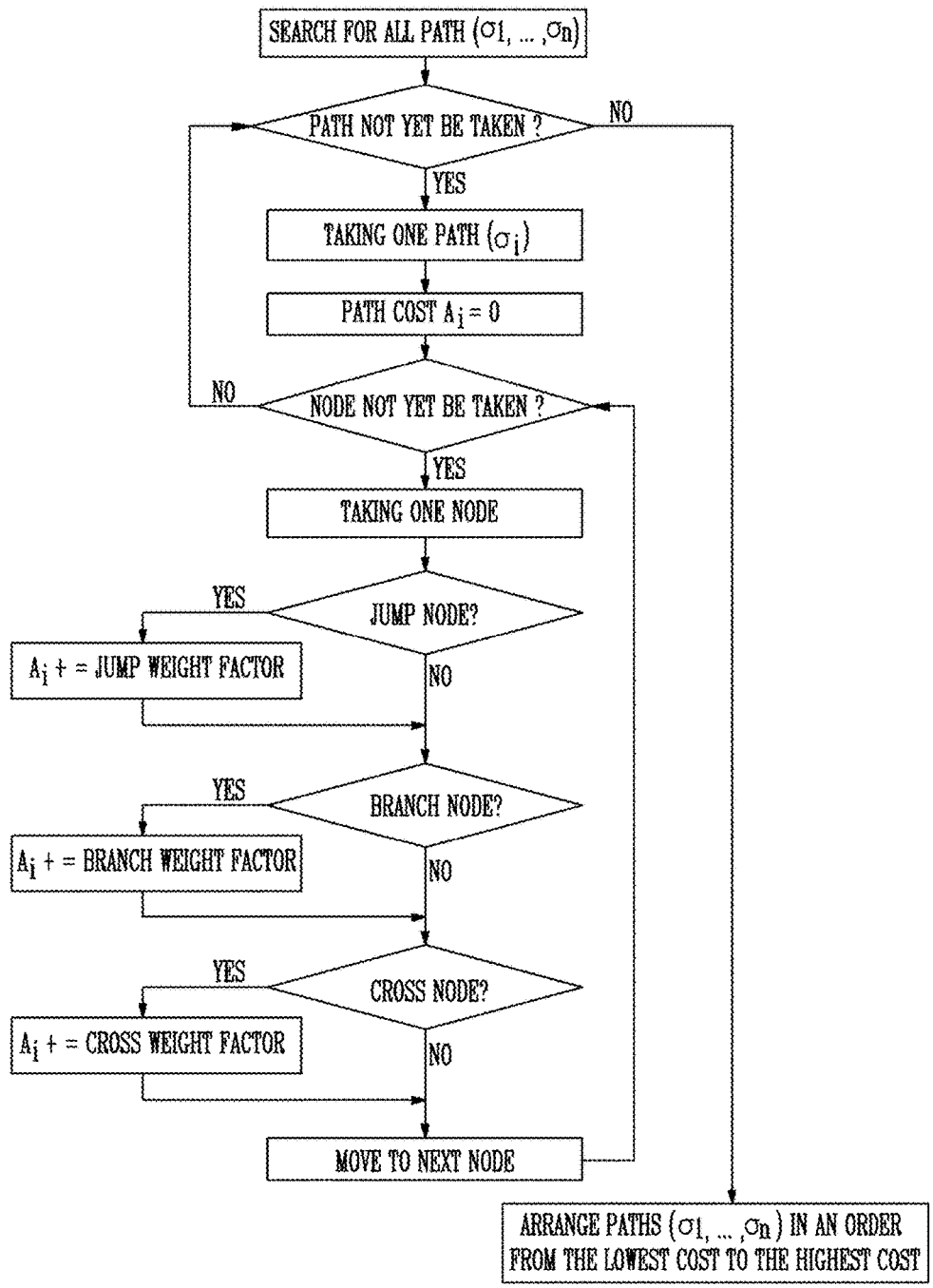
FIG. 4 is a flow diagram of an example algorithm to calculate cost values corresponding to a plurality of candidate paths respectively.
Figure 5A:
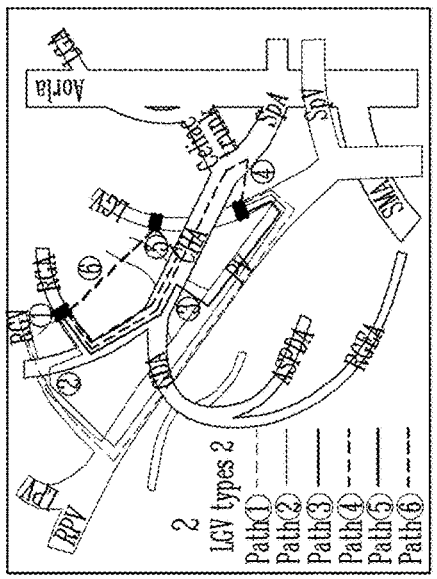
FIGS. 5A, 5B, 5C, and 5D are illustrations of further example operation path recommendations associated with variation-type information.
Figure 5B:
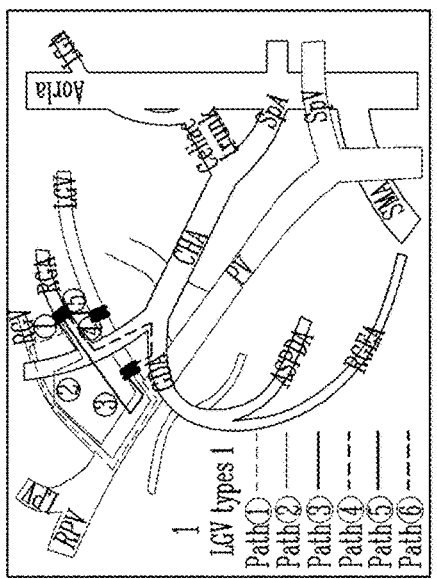
Figure 5C:
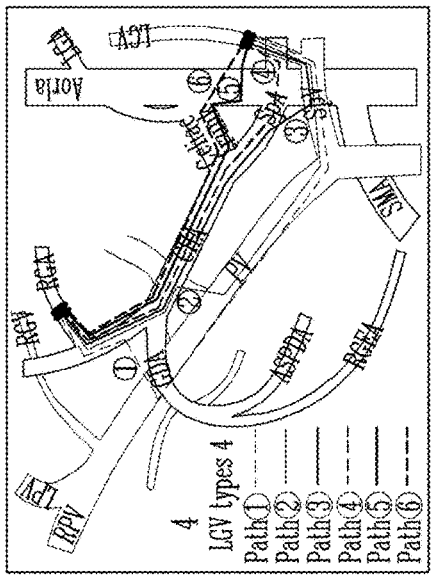
Figure 5D:
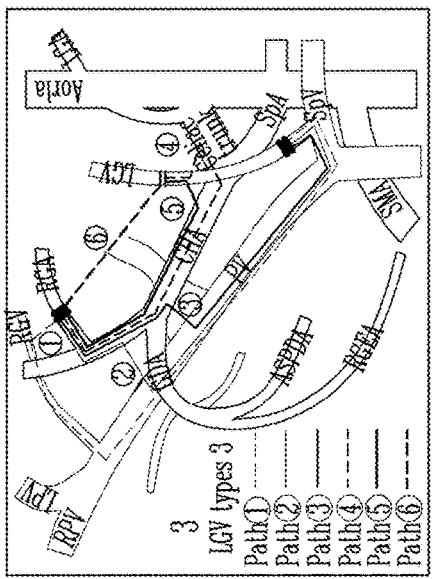

Hereinafter, an operation-path recommendation method and apparatus according to the present disclosure will be described in details with reference to the accompanying drawings. Embodiments to be described below are set forth to provide the skilled person to the art with complete understanding of the present disclosure and, thus, should not be construed to limit the present disclosure thereto. Although elements are diagrammed in the drawings for the sake of clarification, they may be different in a form from those implemented practically.

Although components to embody the present disclosure are described below in a specific way in terms of configurations, such configurations may be exemplified. Thus, the present disclosure may employ different configurations for the components within the scope and spirit thereof. Moreover, each of the components may be implemented either in hardware or in software, while it may be implemented in various combinations thereof as long as achieving the same function. Further, a single hardware or software may implement a combination of two or more components.

It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof.

Now, an operation-path recommendation method according to one embodiment of the present disclosure will be described with reference to FIGS. 1 to 4.

Referring to FIG. 1, an operation-path recommendation method according to one embodiment of the present disclosure may include, (S11) by an operation-path recommendation apparatus, generating a blood vessel graph model based on patient's anatomical information, (S12) by the operation-path recommendation apparatus, extracting a plurality of candidate paths, each path running between defined start and destination points; (S13) by the operation-path recommendation apparatus, extracting node information on at least one node in each of the candidate paths; (S14) by the operation-path recommendation apparatus, applying a cost function to each candidate path, based on the extracted node information; and (S15) by the operation-path recommendation apparatus, recommending an optimal operation path.

The operation-path recommendation apparatus as used herein may be implemented in a variety of types of electronic apparatus to process data and display visual data.

Further, the operation-path recommendation apparatus may be implemented in a single electronic device consisting of hardware and software, or may be implemented in a system where two or more electronic devices may be operatively associated with each other.

Moreover, the operation-path recommendation apparatus may be implemented in a combination of two or more electronic devices linked via wireless or wired communication networks (e.g., one device may act as 'a server device' to process data while the other device may act as 'a display device' to receive and display the processed data). The present disclosure is not limited thereto as different electronic devices alone or in a combination thereof or different system architectures from the above may be taken into consideration to embody the operation-path recommendation apparatus of the present disclosure.

In the step S11, the operation-path recommendation apparatus may generate a blood vessel graph model based on patient's anatomical information.

The 'blood vessel graph model' as used herein may be preferably implemented in a form of a model representing shapes and/or structures of blood vessels using visual elements such as lines, nodes, etc.

In addition, the operation-path recommendation apparatus may preferably acquire patient's anatomical information (blood vessels, organs information, etc.) from patient's image data (for example, CT image data, MRI image data, X-ray image data, ultrasonic image data, etc.). In turn, the operation-path recommendation apparatus may generate a 3D or 2D model based on the acquired patient's anatomical information and then may generate the 'blood vessel graph model' based on the 3D or 2D model.

The 3D model may be first referred to herein. An example process of generating the 'blood vessel graph model' based on the 3D model may be as follows:

First, 1) the operation-path recommendation apparatus may load the patient's image data thereon. 2) The operation-path recommendation apparatus may generate a 3D model for the patient's anatomical information based on the patient's image data. 3) The operation-path recommendation apparatus may generate the blood vessel graph model based on the 3D model.

In the 3D model generation as in the above 2), the operation-path recommendation apparatus may take into consideration selected specific surgical-operation information (or sub-operations information in the specific surgical operation). For example, once the specific surgical-operation is selected, the operation-path recommendation apparatus may specify from an entirety of the anatomical information acquired from the patent's image data only a portion of the anatomical information (e.g., information on blood vessels, organs, etc. within a range to which the selected operation will be applied) associated with the selected specific surgical-operation information. Then, the operation-path recommendation apparatus may generate the 3D model only corresponding to the specified portion of the anatomical information.

Further, in the blood vessel graph model generation as in the above 3), the operation-path recommendation apparatus may reflect viewpoint information of a medical imaging device (e.g., an endoscope, etc.). For example, the operation-path recommendation apparatus may define relative depths among the blood vessels with reference to the viewpoints of the medical imaging device. Therefore, when, from the viewpoints of the medical imaging device, a blood vessel A is positioned above blood vessel B, there may be generated the blood vessel graph model in which the blood vessel B is invisible (or hidden) due to its overlapping with the blood vessel A at an intersection point therebetween.

A reference will be made to FIGS. 2A, 2B, 3A and 3C which are illustrations of generation of the blood vessel graph model based on the 3D model for the patient's anatomical information by the operation-path recommendation apparatus. Specifically, with reference to FIGS. 2A and 2B, there are shown example 3D models generated by the operation-path recommendation apparatus. In turn, with reference to FIGS. 3A and 3B, there are shown example blood vessel graph models generated by the operation-path recommendation apparatus.

The 2D model will be now referred to. An example process of generating the blood vessel graph model based on the 2D model for the patient's anatomical information may be as follows:

First, A) the operation-path recommendation apparatus may load the patient's image data thereon. B) The operation-path recommendation apparatus may generate a 3D model for the patient's anatomical information based on the patient's image data. C) The operation-path recommendation apparatus may generate a 2D model from the 3D model based on the viewpoints information of the medical imaging device. D) The operation-path recommendation apparatus may generate the blood vessel graph model based on the 2D model.

The difference between the above 2D and 3D models employment schemes is that in the 2D model employment scheme, the step of reflecting the viewpoint information of the medical imaging device is separated from the step of generating the blood vessel graph model from the patient's anatomical model (that is, between the 3D model generation and the blood vessel graph model generation, there is intervened the 2D model generation, resulting in more subdivision of the data processing).

In the step S12, the operation-path recommendation apparatus may extract a plurality of candidate paths, where each path runs between defined start and destination points.

In this step, the operation-path recommendation apparatus may automatically define or set the operation-path start and destination points by taking into consideration selected specific surgical-operation information (or sub-operations information in the specific surgical operation). For example, the operation-path recommendation apparatus may extract from a database the start and destination points matching with the specific surgical-operation, and may automatically define or set the extracted points.

Moreover, the operation-path recommendation apparatus may define or set the operation-path start and destination points in a response to user's input information.

Thereafter, the operation-path recommendation apparatus may extract a plurality of candidate operation paths on the blood vessel graph, where each of the candidate operation paths may be configured to run between the start and destination points. Specifically, the operation-path recommendation apparatus may extract the plurality of candidate operation paths on the blood vessel graph, each path being configured to interlink the start and destination points. In this case, the operation-path recommendation apparatus may assign individual identifications to the extracted plurality of candidate paths respectively to distinguish the plurality of candidate paths from one another.

In the step S13, the operation-path recommendation apparatus may extract node information on at least one node contained in each of the candidate paths.

In this step, the operation-path recommendation apparatus may extract a number of nodes or a type of node in each candidate operation path. It may be preferable that the extraction may be carried out for all of the plurality of candidate paths.

Further, the operation-path recommendation apparatus may preferably identify the types of the nodes in each candidate path, for example, a 'jump node', a 'branch node', and/or a 'cross node'. Furthermore, the operation-path recommendation apparatus may preferably extract a number of nodes on a node-type basis. As an example, a number of nodes with a jump node type, a number of nodes with a branch node type, and/or a number of nodes with a cross node type may be extracted respectively. As used herein, the jump node may refer to a node where a transfer between an artery and a vein occurs, the branch node may refer to a node where a plurality of blood vessel is directly coupled to one another, and the cross node may refer to a node where one blood vessel is not visible (or hidden) from a viewpoint of a medical imaging device (e.g., an endoscope, etc.) due to its overlapping with another blood vessel, or vice versa.

The reasons why, in the step S13, the node information on the 'jump node', 'branch node', and/or 'cross node' are particularly extracted amongst a variety of types of nodes is that such nodes may reflect empirical results as follows:

[Empirical Results]

1) The lowest-risk rate method is to follow already-identified blood vessels until it reaches a target point.

2) The more branches the path meets with, the higher the operation risk becomes. When the surgeon encounters a branch in a course of following one blood vessel, he/she should determine which new blood vessel to follow. Such a determination may increase a metal stress of the surgeon and in turn an operation risk since he/she should take into account patient's blood vessel types in the determination.

3) It is preferable that a blood vessel with the lowest invisibility from the viewpoints of the imaging device is assigned the highest priority. When two blood vessels crosses each other, following the blood vessel far away from the viewpoint (the viewpoint of the medical imaging device) may increase operation difficulty and thus operation risk.

4) Since a transfer between an artery and a vein causes a high operation difficulty, and thus high operation risk, it is preferable to select an operation path with the lowest transfer. If the transfer is necessary, it is preferable that the transfer occurs at a location where an artery and a vein are closest to each other.

Specifically, the empirical results 1) and the 2) could be applied to the branch node type, the empirical result 3) could be applied to the cross node type, and the empirical result 4) could be applied to the jump node type. For this reason, in the step S13, the node information on the 'jump node', 'branch node', and/or 'cross node' are particularly extracted or identified amongst a variety of types of nodes.

In the S14, the operation-path recommendation apparatus may apply a cost function (that is, an algorithm to calculate a cost value) to each of the plurality of the candidate operation-paths, based on the extracted node information.

To be specific, in this step, the operation-path recommendation apparatus may calculate a cost value (that is, a value to quantitatively represent a risk rate or stress degree of the operation of interest) for each candidate path, based on the extracted node information for each candidate path.

In this step, in the calculation of the cost value, the operation-path recommendation apparatus may apply a weight factor dependent on a number of the nodes and/or a type of the nodes in each candidate path. For example, 1) the operation-path recommendation apparatus may configure the cost function so that increases of the numbers of the jump nodes, branch nodes and/or cross nodes in each candidate path increase the corresponding cost value. 2) The operation-path recommendation apparatus may configure the cost function so that the weight factor may be dependent on the type of the nodes in each candidate path, that is, the applied weight factors have different values depending on the types of the nodes. The weight factors with different values may be applied between the jump node, the branch node, and the cross node.

Further, the operation-path recommendation apparatus may configure the cost function so that different weight factors may be applied to the nodes with the same node type. To be specific, the different weight factors applied to the nodes with the same node type may be related to an additional characteristic associated with a specific type of the node. For example, 1) when the operation-path recommendation apparatus may apply the weight factor to the jump node, it may further take into account a distance between an artery and a vein. In this case, the additional characteristic may be the distance between an artery and a vein. As an example, the larger distance corresponds to the higher weight factor and thus the larger cost value. 2) When the operation-path recommendation apparatus may apply the weight factor to the cross node, it may further take into account the viewpoint of the medical imaging device. As an example, the blood vessel with the highest invisibility from the viewpoint of the medical imaging device due to its overlapping with another blood vessel at the cross point therebetween may correspond to an applied highest weight factor, while the lowest invisibility may correspond to the applied lowest weight factor.

Now, a reference is made to FIGS. 5A, 5B, 5C, and 5D which shows an algorithm of the example cost function.

As seen in FIGS. 5A, 5B, 5C, and 5D, the cost function may be configured so that the cost value may be calculated on a per-candidate path basis for all of the plurality of candidate paths extracted in the step S12. Further, the cost function may be configured so that the cost value may be calculated to reflect information on a number of nodes and/or a type of the nodes in each candidate path. Specifically, 1) the cost function may be configured so that a larger number of the jump nodes, branch nodes, and/or cross nodes may result in the higher cost value. 2) The cost function may be configured so that the jump node, branch node, and cross node may have different weight factors applied thereto. 3) The cost function may be configured so that, although not specifically shown in FIG. 4, the weight factors applied to the jump nodes may be different based on a distance between an artery and a vein. Further, the cost function may be configured so that, although not shown in FIG. 4, the weight factors applied to the cross nodes may be different based on relative positions from the viewpoint of the medical imaging device. That is, the different weight factors may be applied depending on whether the cross node belongs to the hidden (invisible) or hiding (visible) blood vessels.

After the operation-path recommendation apparatus has calculated the cost values for all of the plurality of candidate paths respectively, it may specify a candidate operation-path with the lowest cost value.

In the cost function as described above, the cost value increases in proportional to increase in operation stress or risk. Thus, the candidate path with the calculated lowest cost value may correspond to the candidate path with the lowest operation stress or risk rate.

In the step S15, the operation-path recommendation apparatus may recommend the optimal operation path to the surgeon.

In this step, the operation-path recommendation apparatus may recommend as the optimal operation path preferably the candidate operation-path with the lowest cost value as specified in the S14 step. Further, the operation-path recommendation apparatus may recommend a multiple (2 or 3) of the candidate operation-paths with the calculated lowest cost value at the same time. In this case, the multiple of the candidate operation-paths with the calculated lowest cost value may be assigned their respective ranks.

In this case, the operation-path recommendation apparatus may provide, in addition to the operation-path recommendations, the cost value calculation results for all of the plurality of the candidate paths extracted in the step S12.

The operation-path recommendation method as described above may take into account the patient's anatomical information to provide the optimal operation path for the specific surgical-operation.

As an example, in case of a lymph node dissection operation, conventionally, the surgeon should determine, in a real time, a progress direction of an operation path from one point of ASPDA (anterior superior pancreaticoduodenal artery) connected to Pancreas to a celiac trunk, by viewing the imaging result of the blood vessel by the medical imaging device. Thus, it may be difficult to effectively avoid the jump node, cross node, and/or branch node, etc. during the operation, leading to increase of the operation stress or risk rate.

However, in accordance with the operation-path recommendation method of the present disclosure, the operation-path recommendation apparatus may recommend the path with the lowest stress or risk rate from among the multiple of the operation paths from one point of ASPDA connected to Pancreas to a celiac trunk. This may lead to improved effectiveness and reliability of the operation.

The operation-path recommendation method of the present disclosure may be implemented into a program product which may be stored in a computer or machine-readable storage medium, or may be distributed in a wireless or wired manner to be downloaded by a variety of types of electronic devices (e.g., a mobile phone, desktop computer, laptop computer, tablets, etc.).

Hereinafter, a reference is made to FIGS. 5A, 5B, 5C, 5D and FIG. 6 which illustrate a path recommendation method according to another embodiment of the present disclosure.

The path recommendation method according to this different embodiment of the present disclosure may further reflect the variation-type information associated with the patient's anatomical information and then may present the operation path information in association with the variation-type information.

Specifically, in the path recommendation method according to this embodiment, the operation-path recommendation apparatus may recommend or provide the operation path principally based on patient's anatomical information, secondarily together with the variation-type information relative to the patient's anatomical information, if any.

For example, the operation-path recommendation apparatus may provide information on a plurality of variation types associated with the patient's anatomical information as in FIGS. 5A, 5B, 5C, and 5D. In this case, the operation-path recommendation apparatus may specify and indicate the variation type belonging to the patient from among the plurality of variation types. In addition, the operation-path recommendation apparatus may extract representative candidate paths for each of the plurality of variation types and may calculate cost values corresponding to the candidate paths respectively. Thus, 'A plurality of candidate paths information', 'Recommended candidate paths information' and/or the like may be provided relative to each of the plurality of variation types.

Furthermore, as illustrated as a table in FIG. 6, the operation-path recommendation apparatus may present, for each of the plurality of variation types, 'Specific cost-value calculation information for the plurality of candidate paths', 'Rank information of the plurality of candidate paths based on cost values', etc.

Now, a reference will be made to FIG. 7 in which an operation-path recommendation apparatus according to one embodiment of the present disclosure is illustrated.

It may be noted that, although an operation-path recommendation apparatus according to one embodiment of the present disclosure, as described below may have a different category from the operation-path recommendation method according to one embodiment of the present disclosure, as described above, the former may have the same or substantially the same (or corresponding) features as the latter. Therefore, the various features as described with reference to the operation-path recommendation method, although not in details described below in order to avoid description repetitions thereof, may be, equally and/or in an inferred manner, applied to the operation-path recommendation apparatus.

Figure 7:
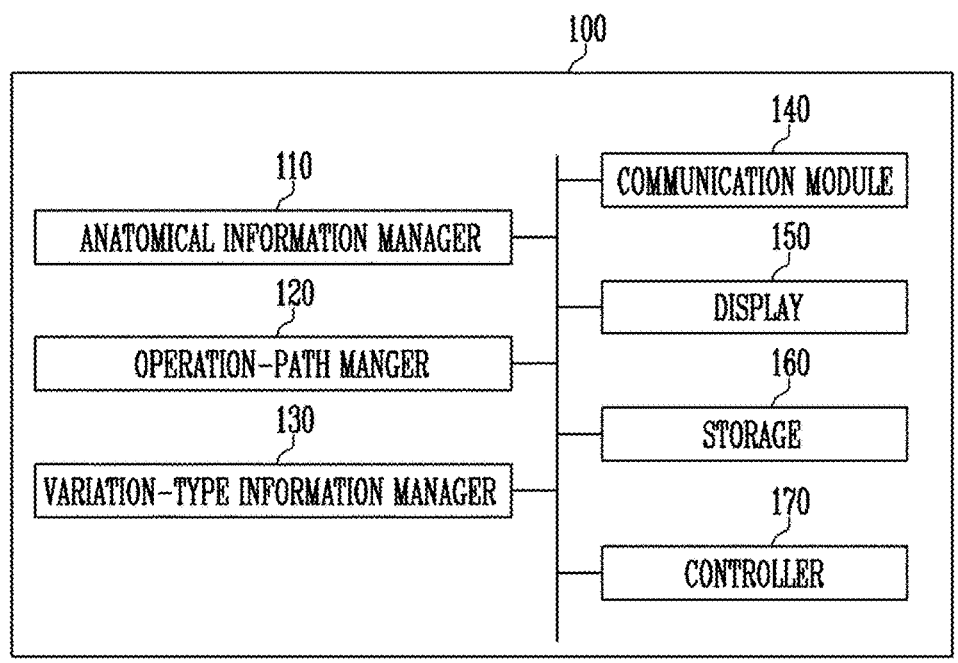
FIG. 7 is a configuration diagram of an operation-path recommendation apparatus, according to one embodiment of the present disclosure.

Referring to FIG. 7, the operation-path recommendation apparatus 100 according to one embodiment of the present disclosure may include an anatomical information manager 110, an operation path manager 120, a variation-type information manager 130, a communication module 140, a display 150, a storage 160, and a controller 170. The present disclosure is not limited thereto, but this apparatus 100 may further include other components than as listed herein.

It may be noted that, as mentioned above, each of the components may be implemented either in hardware or in software, while it may be implemented in various combinations thereof as long as achieving the same function. Further, a single hardware or software may implement a combination of two or more components.

The anatomical information manager 110 may be configured to manage the patient's anatomical information. The anatomical information manager 110 may be configured to manage image data representing the patient's anatomical information. In addition to this function, the manager 100 may perform a variety of functions as described above with connection to the patient's anatomical information.

The operation path manager 120 may be configured to generate the blood vessel graph model based on the anatomical information, to extract the plurality of candidate paths between the defined start point and destination point, to extract the node information on at least one node in each of the extracted candidate paths, and to apply a cost function to each candidate path based on the node information.

The operation path manager 120 may be configured to generate the 3D model for the patient's anatomical information based on the patient's image data, and to generate the blood vessel graph model based on the generated 3D model.

Further, the operation path manager 120 may be configured to define or set start and destination points associated with the selected specific surgical-operation, and to extract, on the blood vessel graph model, the plurality of candidate paths between the defined start and destination points.

Furthermore, the operation path manager 120 may be configured to extract a number of and/or a type of at least one node in each of the extracted candidate paths.

In addition, the operation path manager 120 may be configured to take into account the information on the number of and/or the type of at least one node in each of the extracted candidate paths, to calculate cost values corresponding to the candidate paths respectively, and to specify and recommend as an optimal path the candidate path with the lowest cost value from among the plurality of candidate paths.

It may be understood that the operation path manager 120 may be further configured to perform, in addition to these functions, the variety of functions as described above in connection with the operation path recommendations.

The variation-type information manager 130 may be configured to manage information on the variation types associated with the patient's anatomical information managed by the anatomical information manager 110.

The variation-type information manager 130 may be further configured to determine and store whether the variation types associated with the patient's anatomy exist or not, and, if so, to determine and store what variation type the patient's anatomy belongs to, and to determine and store what variation types are different from the variation type of the patient's anatomy, and so on. It may be appreciated that the variation-type information manager 130 may be further configured to perform, in addition to these functions, the variety of functions as described above in connection with the variation type.

The communication module 140 may be configured to communicate data with a variety of electronic devices. The communication module 140 may be connected via wired or wireless networks to the variety of electronic devices such as a medical surgery device, a medical diagnostic device, or the like, to communicate various data used in the operation path recommendation with the variety of electronic devices.

It may be appreciated that the communication module 140 may include a variety of standards of wireless or wired communication modules.

The display 150 may be configured to display various data used in the operation path recommendation. It may be understood that the display 150 may be implemented in various types of display modules.

The storage 160 may be configured to store therein various data used in the operation path recommendation. It may be understood that the storage 160 may include a variety of types of memory devices. The storage 160 may store therein, for example, the patient's anatomical information, the 3D model or 2D model, the blood vessel graph model, the plurality of candidate path information, the cost function information, the calculated cost value information, the specified recommendation path information, the variation-type information, to name a few.

The controller 170 may be configured to control the anatomical information manager 110, the operation path manager 120, the variation-type information manager 130, the communication module 140, the display 150, and/or the storage 160. That is, the controller 170 may be configured to control the variety of acts or functions of components of the operation-path recommendation apparatus 100.

The controller 170 may include at least one computing device. The computing device may include, but not be limited to, a general purpose central processing unit (CPU), a special purpose-implemented programmable device (CPLD (Complex Programmable Logic Device), FPGA (field programmable gate array)), an application-specific integrated circuit (ASIC) and/or a microcontroller chip, to name a few.

Example embodiments of the present disclosure have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A method for determining an intravenous pathway for a surgical instrument, the method comprising:
   generating a blood vessel graph model based on a patient's anatomical information;
   defining at least one start point and at least one destination point for the intravenous pathway;
   determining a number of jump nodes, a number of branch nodes, and a number of cross nodes in each candidate path; and
   determining an optimal path from among the candidate surgical paths based on the number of jump nodes, the number of branch nodes, and the number of cross nodes in each candidate path,
   wherein the jump node is a location along the pathway in which the pathway transfers from an artery to a vein, or transfers from a vein to an artery, the branch node is a location along the pathway at which a single vein or artery branches into a plurality of veins or arteries, and the cross node is a location along the pathway at which the pathway passes in front of or behind a vein or an artery.

2. The method of claim 1, wherein the (a) comprises:
   loading patient's image data thereon;
   generating a 3-dimensional (3D) model for the patient's anatomical information, based on the patient's image data; and
   generating the blood vessel graph model based on the 3D model.

3. The method of claim 2, wherein the anatomical information includes viewpoint information of an imaging device imaging the patient's image data.

4. The method of claim 1, wherein the method further comprises:
   calculating cost values for each of the plurality of candidate paths; and
   identifying a candidate path with the lowest cost value from the plurality of candidate paths as an optimum path.

5. The method of claim 4, wherein the method further comprises applying a weight factor to a cost value for each candidate path, the weight factor being dependent on a type of a node in each candidate path.

6. A non-transitory electronic machine-readable storage medium including a program therein, the program being configured to, when executed by an electronic machine, cause the machine to perform a method of determining a pathway for a surgical instrument, the method comprising:

generating a blood vessel graph model based on a patient's anatomical information;

extracting a plurality of candidate surgical paths, each path running between defined start and destination points;

determining a number of jump nodes, a number of branch nodes, and a number of cross nodes in each candidate path; and determining an optimal path from among the candidate surgical paths based on the number of jump nodes, the number of branch nodes, and the number of cross nodes in each candidate path, wherein the jump node is a location along the pathway in which the pathway transfers from an artery to a vein, or transfers from a vein to an artery, the branch node is a location along the pathway at which a single vein or artery branches into a plurality of veins or arteries, and the cross node is a location along the pathway at which the pathway passes in front of or behind a vein or an artery.

* * * * *